(12) United States Patent
Dupuis et al.

(10) Patent No.: US 8,703,154 B2
(45) Date of Patent: Apr. 22, 2014

(54) ADJUVANT FOR THE PREPARATION OF VACCINE COMPOSITIONS INTENDED FOR THE PREVENTION OF COCCIDIOSIS

(75) Inventors: Laurent Dupuis, Reims (FR); Francois Bertrand, Boulogne Billancourt (FR); Sebastien Deville, Paris (FR)

(73) Assignee: Societe d'Exploitation de Produits pour les Industries Chimiques SEPPIC, Paris (FR)

( * ) Notice: Subject to any disclaimer, the term of this patent is extended or adjusted under 35 U.S.C. 154(b) by 0 days.

(21) Appl. No.: 13/575,971

(22) PCT Filed: Jan. 14, 2011

(86) PCT No.: PCT/FR2011/050069
§ 371 (c)(1),
(2), (4) Date: Jul. 30, 2012

(87) PCT Pub. No.: WO2011/092413
PCT Pub. Date: Aug. 4, 2011

(65) Prior Publication Data
US 2012/0308604 A1    Dec. 6, 2012

(30) Foreign Application Priority Data

Feb. 1, 2010   (FR) ...................... 10 50663

(51) Int. Cl.
*A61K 39/39* (2006.01)
*A61K 39/012* (2006.01)

(52) U.S. Cl.
USPC ................... 424/283.1; 424/271.1; 424/278.1

(58) Field of Classification Search
None
See application file for complete search history.

(56) References Cited

FOREIGN PATENT DOCUMENTS

WO    2005/009462    2/2005
WO    2006081826    8/2006

OTHER PUBLICATIONS

International Search Report dated Apr. 27, 2011, in corresponding PCT application.

Anonymous: "Marcol 52", Exxon Mobil, 2007, pp. 1-3, XP002599991, Retrieved from the Internet: URL:http://www.exxonmobil.com/UK-English/Specialties/PDS/glxxenspcemmarcol52.pdf, p. 2.
Anonymous: "Marcol 82". Exxon Mobil, 2007, pp. 1-3, XP002599992, Retrieved from the Internet: URL:http://www.exxonmobil.com/UK-English/Specialties/PDS/glxxenspcemmarcol82.pdf, p. 2.
Ding Xicheng et al: "Protective immunity against *Eimeria acervulina* following in ovo immunization with a recombinant subunit vaccine and cytokine genes", Infection and Immunity, vol. 72, No. 12, Dec. 2004, pp. 6939-6944. XP002600560.
Dupuis L. et al: "SEPPIC vaccine adjuvants for poultry.", Annals of the New York Academy of Sciences, vol. 1081, Oct. 2006, pp. 202-205. XP002599990.
Piretti M. V. et al: "Investigation of the Hydro Carbons Found in the Tissues of Chickens Injected With Inactivated Oil Adjuvant Vaccine", Zeitschrift Fuer Lebensmittel-untersuchung Und—Forschung, vol. 175, No. 4, 1982, pp. 245-248. XP002599989.
Duncan E. S. Stewart-Tull: "The Use of Adjuvants in Experimental Vaccines. II. Water-in-Oil Emulsions: Freund's Complete and Incomplete Adjuvants", Methods in Molecular Medicine, vol. 4, Jan. 1, 2003, pp. 141-145. XP001525280. Humana Press, Totowa, NJ, US.
Aucouturier Jerome et al: "Montanide ISA 720 and 51: a new generation of water in oil emulsions as adjuvants for human vaccines", Expert Review of Vaccines, vol. 1, No. 1, Jun. 1, 2002, pp. 111-118. XP002262967. Future Drugs, London, GB.
Kuroda Yoshiki et al: "Distinctive patterns of autoimmune response induced by different types of mineral oil", Toxicological Sciences, vol. 78, No. 2, Apr. 2004, pp. 222-228. XP002599988.
Stewart-Tull Duncan E. S.: "Freund's complete and incomplete adjuvants, preparation, and quality control standards for experimental laboratory animals use", Methods in Molecular Biology, Humana Press Inc. NJ, US, vol. 626, Jan. 1, 2010, pp. 59-72. XP001525277.
Iseki Kanako et al: "Evaluation of a new oil adjuvant for use in peptide-based cancer vaccination.", Cancer Science Oct. 2010 LNKD-DOI:10.1111/J.1349-7006.2010.01653.X PUBMED:20678155, vol. 101, No. 10, Oct. 2010, pp. 2110-2114, XP002631708.

*Primary Examiner* — Padma V Baskar
(74) *Attorney, Agent, or Firm* — Young & Thompson

(57) ABSTRACT

A vaccine adjuvant which, based on the 100% mass thereof, includes between 10% and 95% of a mineral oil containing: between 0.05 mass-% and 10 mass-% hydrocarbon chains having less than 16 carbon atoms, and between 0.05 mass-% and 5 mass-% hydrocarbon chains having more than 28 carbon atoms. In addition, the adjuvant has a P/N ratio, corresponding to the ratio of the mass quantity of the paraffinic hydrocarbon chains to the mass quantity of the naphthenic hydrocarbon chains, of between 2.5 and 3, the adjuvant being intended for the production of a vaccine composition to prevent coccidiosis.

2 Claims, No Drawings

ADJUVANT FOR THE PREPARATION OF VACCINE COMPOSITIONS INTENDED FOR THE PREVENTION OF COCCIDIOSIS

The present invention relates to novel adjuvants for the preparation of vaccine compositions intended for the prevention of coccidiosis in poultry, vaccine compositions comprising said adjuvants and the use of a specific mineral oil for the manufacture of said adjuvant.

Coccidioses are frequent parasitic diseases in poultry.

Poultry are domestic birds generally belonging to the gallinaceous or palmiped birds that are farmed for their meat or their eggs either in a traditional farmyard or by factory farming.

The expression poultry is understood to mean: chicken, turkey, goose, duck, guinea fowl, pigeon, quail, pheasant, ostrich.

The etiological agent (or carrier of the disease) is an intracellular protozoan parasite which is called coccidium, and belonging most often to the genus *Eimeria*.

There are several types of coccidia for each avian species:
Chicken coccidia: *E. acervulina, E. necatrix, E. maxima, E. brunetti, E. tenella, E. mitis, E. praecox.*
Turkey coccidia: *E. meleagrimitis, E. adenoeides, E. dispersa, E. gallopavonis.*
Goose coccidia: *E. truncata* (it can also affect musk duck and swan), *E. anseris.*
Duck coccidia: *Tyzzeria perniciosa, E. mulardi.* The disease affects in particular mulard duck.
Guinea fowl coccidia: *E. numidia, E. grenieri* (the most frequent but of lower pathogenicity).
Pigeon coccidia: *E. labbeana*

The prevention of coccidiosis is based on the following solutions:

a) A Chemo-Prevention Method:

This method uses chemical compounds of the antibiotic type and has as disadvantages:
- generating risks of developing allergies in animals treated with these antibiotics, in particular because of the presence of "residues" or of undesirable by-products in these antibiotics;
- generating risks of developing resistance to antibiotics in the treated species;
- being governed by restrictive regulations;
- damaging the image of commercial poultry meat, with the risk of no longer having the benefit of quality labels claiming breeding under "natural" conditions.

b) A Vaccination Method Involving "Live" Vaccines:

Vaccines obtained from attenuated live agents are prepared by multiplying the infectious agents in a laboratory until they lose naturally or artificially, by mutation, their pathogenic character.

The strains obtained are then incapable of fully developing the disease which they previously caused.

These strains however preserve their antigens, and their capacity to induce immune responses.

This mode of vaccination makes it possible, after administration to animals, to colonize the digestive tracts and to avoid implantation of strains with virulence factors.

This mode of vaccination has as disadvantages:
- possible return to virulence;
- the need to carry out large-scale cultures of potentially pathogenic bacteria;
- the animals vaccinated by this method may excrete, thus constituting a potentially pathogenic source in the environment and therefore potential for dissemination of these pathogens.

The latter disadvantage therefore constitutes one reason why it is not preferred in the case of open air breeding of poultry for vaccinating against coccidiosis which is a parasitic disease and therefore easily transmissible by dissemination.

Anticoccidial vaccines are veterinary medicaments. As a result, they are subject to legislation which applies to veterinary medicaments, which itself depends on the legislation on medicaments.

Three anticoccidial vaccines are authorized in France: they are live vaccines consisting of "early" strains which are attenuated by immunogenic and protective against species found in the field.

These three vaccines can only be used for the fowl species (*Gallus gallus*) because they only contain species capable of parasitizing this bird species, there is no cross-immunity against different species of coccidia.

c) The Conventional Methods of Vaccination with a Non-living or "Inactivated" Antigen:

The efficacy of existing vaccines are not satisfactory because the level of the cellular component of the immune response is not sufficiently high to induce effective protection in the specific case of parasitic diseases such as coccidiosis in particular.

Many cDNAs encoding *Eimeria* antigens have been described, and immunization trials are underway with some of them. The development of resistance also depends on the genetic background and the mode of administration (and on the adjuvant). Some antigens have shown partial protection. The research relates to antigens common to several species of coccidia: for example the GX3262 antigen which is reactive with a monoclonal antibody which recognizes a sporozoite antigen that is common to seven species of chicken coccidia, induces partial protection.

There is therefore a need to improve these inactivated vaccine compositions.

The development of inactivated vaccines or vaccines containing purified antigens is increasingly important because it makes it possible to avoid as much as possible undesirable side effects in the vaccinated subjects before and after vaccination. However, improving the quality of the antigens is achieved at the expense of their immunogenicity. It is for this reason that they are combined with adjuvants which make it possible to increase the immune response in the vaccinated subjects.

These adjuvants are diverse in nature. They may for example consist of liposomes, emulsions comprising at least one oily phase and at least one aqueous phase, of the so-called Freund's adjuvant type, more commonly of water-insoluble inorganic salts. Among the inorganic salts used as adjuvants for vaccine compositions, there may be mentioned for example aluminum hydroxide, cerium nitrate, zinc sulfate, colloidal iron hydroxide or calcium chloride. Aluminum hydroxide is the adjuvant most commonly used. These inorganic salts used as adjuvants for vaccine compositions are described in particular in the article by Rajesh K. Gupta and al "Adjuvants, balance between toxicity and adjuvanticity", Vaccine, vol. 11, Issue 3, 1993, pages 993-306.

The adjuvants mentioned above have as disadvantage a low efficacy. In addition, it is known that aluminum hydroxide only efficiently induces humoral immunity, and not cellular immunity. Moreover, they can induce some toxicity toward the treated subjects. More particularly, when these vaccine compositions are injected into the subjects to be vaccinated, it is possible to observe the formation of lesions and other local reactions such as granulomas at the site of injection.

Other adjuvants, consisting of divalent or trivalent metal salts or else of sympathomimetic compounds are described respectively in international patent applications published under the numbers WO 96/32964, WO 98/17311 and WO 98/15288.

Emulsions are stable mixtures consisting of a system of two immiscible liquids one of which is divided into droplets in the other. Thus, emulsions comprise oils, an aqueous phase and surfactants which have the role of dispersing one of the two phases in the other and of obtaining a macroscopically homogeneous and stable mixture. They are often used as immunity adjuvants in vaccine formulations. The use of mineral oils as vaccine adjuvant has been known for many years (Freund 1956, Herbert 1967). The mineral oils used as vaccine adjuvants are liquid hydrocarbons which are obtained by distillation of petroleum and by the use of subsequent treatment steps such as for example steps of desulfurization, of deasphalting, of extraction of aromatic compounds, of extraction of waxes, and other finishing treatment steps. Studies of the influence of the quality of oils on the immune response only came about gradually and in an incomplete manner. Indeed, the composition of mineral oils is greatly influenced by the geographic origin of the crude oils used and of the process (chemistry and equipment) used for their preparation. Studies carried out on the various fractions were intended to evaluate the toxic nature for workers, users, but not for uses in animal or human health). Optimizations of the composition of these mineral oils, based on macroscopic characterizations (viscosity, melting point) were carried out with grades of existing industrial mineral oils, or of pure laboratory chemical products not corresponding to definitions or to the characterization of grades of acceptable raw materials. Thus, even extensive studies carried out on industrial grades of mineral oils defined by parameters not reflecting their biological properties caused and still cause variations in behavior during use for vaccines depending on the origin of a batch of mineral oil. These batches, although corresponding to their macroscopic analytical requirements and specifications and having the same trade name, have compositions which are sufficiently different so as not to give the same properties for the vaccines. Moreover, the viscosity of the emulsions obtained from mineral oils, without galenic optimization, induced a bias in the interpretation of the results.

The influence of the distribution between linear and cyclized chains was evaluated in order to assess potential toxicity during the use of the mineral oils by injection suspecting the teratogenic role of the cyclized forms. The criteria for toxicity were then identified as coming from the unsaturated forms, which are completely removed in current processes by extensive hydrogenation.

No study has been carried out with the aim of evaluating the influence of the ratio of constituents of the linear or cyclized type on the quality of the immune response.

Mineral oils have been used for many decades as adjuvants and for the preparation of adjuvants intended to increase the efficacy of the immune response of vaccines. Indeed, antigens emulsified beforehand in emulsions of the water-in-mineral oil (W/O) type and then administered by the parenteral route initiate immune responses (and consequently protections against pathogens) which are much more intense and lasting. The nature of the mineral oil used for the preparation of adjuvants has a strong influence on the intensity of the immunological response and on the secondary reactions linked to the injection of the vaccine (local and general reactions).

There are two types of immune responses:

The Humoral Immune Response:

It is the reaction which is produced when the B lymphocytes possessing specific receptors are stimulated by an antigen and differentiate into a clone of plasmocytes which start to secrete antibodies. These are effective against the pathogenic agents circulating in the blood and the lymph. Furthermore, the selective activation of the B lymphocytes endows the organism with memory cells with an extended life which intervene in the secondary immune response, and The Cellular Immune Response The humoral immune reaction helps the defense network to recognize and destroy the free pathogenic agents, but it is the cell-mediated reaction which combats the pathogenic agents already introduced into the cells. The main actors of cell-mediated immunity are the T lymphocytes.

The T lymphocutes only react to the antigenic determinants exposed at the surface of the cells of the organism. The T lymphocytes recognize these determinants by virtue of their receptors, surface proteins embedded in their plasma membrane. The receptor for the T lymphocyte recognizes the antigen combined with one of the glycoproteins of the MHC of the organism. In addition to their role in the humoral response, the helper T lymphocytes can also activate other types of T lymphocyte in order to initiate the cell-mediate reactions against antigens. The cytotoxic T lymphocytes are the only cells that kill other cells (cells infected with intracellular pathogenic agents).

The oily adjuvants are well known for increasing the humoral component of the immunological response (measured in general by assays of immunoglobulins of group 1 or IGG1) whereas cellular type responses (indirectly measured by the IGG2s) are very difficult to obtain.

It is known that W/O emulsions, which give the strongest immune responses, also induce a cellular-type component but in lower proportions, for example, than some soluble molecules (saponin or cationic surfactant type) which are reputed to orient the response toward cellular mechanisms.

Emulsions with an aqueous continuous phase using the mineral oils typically on the market are very poor promoters of cellular response.

Indeed, the type of response produced by the vaccines is influenced by the structure of the antigen, but also by the way the latter is presented to the immune system via the adjuvants. The adjuvants have different effects on the immune response because they can induce an immune response over a longer or shorter period, with a predominant character of the cellular type or of the humoral type.

Cell-mediate immunity is important, or even sometimes essential for protection against intracellular bacteria, viruses and most parasites. It is involved in most vaccine protection mechanisms as a supplement to the humoral response.

It is for example possible to classify the capacity of an adjuvant to induce a cellular-type immunological response for the vaccine composition comprising it by comparing the IGG1/IGG2 ratios measured following the parenteral administration of the vaccine composition comprising it to the relevant subjects, at different periods following the day of vaccination of said subjects. The higher this ratio, the more the adjuvant will have oriented the immune response of the vaccine composition toward a humoral component. A value of the IGG1/IGG2 ratio close to one will be considered as the sign of a balanced immune response of the vaccine composition between its two components. A value of the IGG1/IGG2 ratio of less than one will be characteristic of an immune response of the vaccine composition that is predominantly cellular.

One aim of the present invention is to have available an adjuvant for the preparation of vaccine compositions, which is intended to improve the cellular component of the immune response, while maintaining a good level of the humoral component. There is therefore a need to obtain vaccine adjuvants having a balanced immune response or that is even predominantly cellular. In addition, the vaccines prepared with the adjuvant which is the subject of the present invention should exhibit good safety.

To this end, the subject of the present invention is a vaccine adjuvant comprising for 100% of its mass:
from 10% to 95%, and preferably from 20% to 90%, of a mineral oil comprising:
from 0.05 mass % to 10 mass % of hydrocarbon chains having less than 16 carbon atoms;
from 0.05 mass % to 5 mass % of hydrocarbon chains having more than 28 carbon atoms;
and having a P/N ratio, corresponding to the ratio between the quantity by mass of hydrocarbon chains of the paraffin type and the quantity by mass of hydrocarbon chains of the naphthene type, of between 2.5 and 3,
for the manufacture of a vaccine composition intended for the prevention of coccidiosis.

Moreover, embodiments of the invention may comprise one or more of the following characteristics:
Adjuvant as defined above, for the manufacture of a vaccine composition intended for the prevention of coccidiosis in animals, in particular poultry.
Adjuvant as defined above, characterized in that said P/N ratio is between 2.5 and 3, preferably between 2.8 and 2.9.
Adjuvant as defined above, characterized in that it additionally comprises:
from 5% to 90% of at least one surfactant. Preferably from 5% to 50%.

According to another aspect, the subject of the invention is a vaccine intended for the prevention of coccidiosis, comprising the adjuvant as defined above and at least one antigen.

Moreover, embodiments of the invention may comprise one or more of the following characteristics:
vaccine as defined above, intended for the prevention of coccidiosis in animals, in particular poultry,
vaccine as defined above, characterized in that the coccidia are chosen from the group consisting of *Eimeria, Isospora, Toxoplasma, Besnoitia, Neospora*, preferably *Eimera*,
vaccine as defined above, characterized in that it is in the form of an emulsion of the water-in-oil (W/O) type, and
vaccine as defined above, characterized in that the antigen is a recombinant protein containing the *Eimera Acervulina* sequence 3-1.

According to another aspect, the subject of the invention is the use of a mineral oil for the manufacture of a vaccine as defined above, characterized in that said oil comprises for 100% of its mass:
from 0.05% to 10% of hydrocarbon chains having less than 16 carbon atoms;
from 0.05% to 5% of hydrocarbon chains having more than 28 carbon atoms;
and has a P/N ratio, corresponding to the ratio between the quantity by mass of carbon chains of the paraffin type and the quantity by mass of carbon chains of the naphthene type, of between 2.5 and 3, preferably between 2.8 and 2.9.

The composition according to the invention may also advantageously contain one or more emulsifying surfactants. The latter exhibit a lipophilic or hydrophilic character characterized by an HLB (hydrophilic-lipophilic balance) value of between 1 and 19.

Such a surfactant may consist of
an alkylpolyglycoside or a mixture of alkylpolyglycosides of formula $R_a$—(O)—Zn where $R_a$ represents a linear or branched saturated aliphatic radical comprising from 4 to 24 carbon atoms, Z is the residue of a sugar, preferably glucose, and n is between 1 and 5, preferably between 1.1 and 2,
saponins,
sorbitan esters, such as for example sorbitan oleate, sorbitan stearate, sorbitan palmitate, sorbitan laurate;
mannitan esters, such as for example mannitan oleate, mannitan stearate, mannitan palmitate, mannitan laurate;
polyoxyethylated sorbitan esters between 5 moles and 20 moles of ethylene oxide, such as for example ethoxylated sorbitan oleate containing 20 moles of ethylene oxide;
polyoxyethylated mannitan esters between 5 moles and 20 moles of ethylene oxide, such as for example ethoxylated mannitan oleates containing 20 moles of ethylene oxide;
lecithins;
polyoxyethylated alkanols such as for example those marketed under the name BRIJ, and more particularly BRIJ 21 and BRIJ 221 by the company UNIQEMA;
surfactant polymers comprising polyoxyethylenated and polyoxypropylenated blocks, such as those marketed under the name PLURONICS by the company BASF;
polyglycol or polyglycerol polyhydroxystearates such as for example the products called HYPERMER™ B246, ARLACEL™ P135 marketed by the company UNIQEMA.

The expression antigen is understood to mean any molecule having immunogenic properties which are capable of inducing a specific immune response. These antigens may be inactivated pathogens, such as for example inactivated bacteria, molecules extracted from pathogens, molecules produced by genetic recombination of microorganisms.

Mineral oils are obtained from distillation, followed by extensive hydrogenation of products of petroleum origin. They consist of chemical molecules of the saturated alkane family. For this type of molecules, the number of carbon atoms (n) is in general greater than 9 and less than 30, thereby conferring a liquid appearance at 25° C. The expression liquid paraffin is also used. Solid paraffins consist of chemical molecules of the alkane family for which n is greater than 30, may range up to 50, and thereby confer a solid appearance at 25° C. Liquid paraffins, or mineral oils, are transparent and odorless liquids whose dynamic viscosity may vary from 2 milliPascal.seconds (mPa.S) to 1 Pascal.second. The dynamic viscosity of mineral oils is directly linked to the mean length of the carbon chains of alkanes which constitute said mineral oils. Alkanes with the longest hydrocarbon chains are responsible for the highest dynamic viscosities. The molecules involved may be in the form of branched linear or hydrocarbon linear chains (grouped under the name "paraffin" (P) or cyclized (naphthene N)) but still saturated (without double bonds which are eliminated during hydrogenation treatment). The viscosities, melting points and boiling points are directly linked to the number of carbons which the hydrocarbon chain contains. A white mineral oil can therefore be characterized by its distillation range, its dynamic viscosity, its average number of carbon atoms, but also by its P/N ratio between the linear and branched molecules and the quantity of cyclized molecules (determined according to the DIN 51378 method). It should be noted that the dynamic viscosity criterion may be artificially modified by mixing two different cuts.

EXAMPLES

I) Part One

The following examples make it possible to demonstrate the properties of the adjuvant compositions according to the present invention.

In this work, a study of the adjuvant properties of various finely characterized oils has made it possible to identify novel original compositions characterized by limits of compositions established by chromatography.

The study carried out on experimental vaccine compositions in a first instance with formulas provided in the form of water-in-oil (W/O) emulsions has made it possible to establish optimum conditions for obtaining balanced immune responses between its two components and an immune response with a predominant cellular component for formulas that are well tolerated in mice. The next phase of the experimental trials, carried out on other types of formulas and different animals, has made it possible to demonstrate that the adjuvant compositions which are the subject of the present invention provide the best immunological responses both quantitatively and qualitatively. In the examples which follow, the mineral oils selected are characterized by their:

short fraction (SF) expressed in percent, corresponding to the proportion of entities having a number of carbon atoms C<16.
heavy fraction (HF) expressed in percent, corresponding to the proportion of entities having a number of carbon atoms C>28.
molecular distribution (MD) (expressed as number of carbon atoms C) calculated as the barycentre of the curve between C16 and C28 by attributing the surface coefficient of the fractions C16 to C20 assimilated to 18 carbon atoms, 20 carbon atoms to 24 carbon atoms assimilated to 22 carbon atoms and 24 carbon atoms to C28 assimilated to 26 C.
P/N ratio (obtained according to the standard method DIN 51378).

The various oils tested are listed in table 1.

TABLE 1

Panel of oils synthesized and characterized for biological trials.

| Oil ref | SF (<C16) | MD | HF (>C28) | P/N |
|---|---|---|---|---|
| 1 | 13.7 | 20.6 | 3.3 | 1.78 |
| 2 | 4.9 | 21.5 | 7.1 | 1.86 |
| 3 | 4.2 | 20.5 | 1.5 | 1.86 |
| 4 | 4.4 | 21.6 | 4.7 | 1.86 |
| 5 | 47.7 | 18.4 | 0.5 | 1.86 |
| 6 | 0.3 | 22.2 | 9.6 | 2.03 |
| 7 | 30 | 18.3 | 0.6 | 2.19 |
| 8 | 16 | 21.8 | 10 | 2.13 |
| 9 | 2 | 19.3 | 2.2 | 2.85 |
| 10 | 48.2 | 18.4 | 0.6 | 1.86 |
| 11 | 8.6 | 20.7 | 2.4 | 1.94 |
| 12 | 20.8 | 21.9 | 8.7 | 1.86 |

Study in the Form of a Water-in-Oil W/O Emulsion

The formulation is made in an incomplete Freund's adjuvant (IFA) type model used at 50% in the vaccine emulsion which by virtue of the simplicity of its formula (mannide monooleate 15%+mineral oil 85%) allows an appropriate comparison.

The biological properties of the vaccines thus formulated (50% IFA+50% of the isotonic solution of egg albumin at 10 µg/dose; 1 dose=100 µl of emulsion) were then compared in the mouse model for the parameters of safety (table 2) and of efficacy for the humoral or cellular response.

The safety is evaluated by observing the site of injection 7 days after vaccination and then scoring the local reactions (LR) on a scale ranging from 0 to 4. The values from 0 to 2 are acceptable (this is the maximum oily deposit without alopecia, no palpable induration or visible site of injection); values greater than 2 are considered undesirable and inacceptable (this involves necrosis, alopecia, palpable induration). The results are grouped together in table 2; the mineral oils tested in the preparation of the W/O formulation were classified according to their SF. It is clearly apparent that the W/O formulations comprising mineral oils having an SF<13.7 are appropriate for the preparation of vaccine compositions that can be used for injection.

TABLE 2 evaluation of the safety of the various oils.

| Oil ref | SF (<C16) | MD | HF (>C28) | P/N | LR |
|---|---|---|---|---|---|
| 1 | 13.7 | 20.6 | 3.3 | 1.78 | 2.5 |
| 2 | 4.9 | 21.5 | 7.1 | 1.86 | 0.5 |
| 3 | 4.2 | 20.5 | 1.5 | 1.86 | 0 |
| 4 | 4.4 | 21.6 | 4.7 | 1.86 | 0.5 |
| 5 | 47.7 | 18.4 | 0.5 | 1.86 | 4 |
| 6 | 0.3 | 22.2 | 9.6 | 2.03 | 0 |
| 7 | 30 | 18.3 | 0.6 | 2.19 | 3 |
| 8 | 16 | 21.8 | 10 | 2.13 | 2.5 |
| 9 | 2 | 19.3 | 2.2 | 2.85 | 0 |
| 10 | 48.2 | 18.4 | 0.6 | 1.86 | 4 |
| 11 | 8.6 | 20.7 | 2.4 | 1.94 | 0.5 |
| 12 | 20.8 | 21.9 | 8.7 | 1.86 | 3 |

The formulas selected were then tested for their immunological efficacy in the mouse model. The formulas giving inacceptable reactions were eliminated. Tables 3 and 4 show the antibody titers obtained, compared with an aluminum hydroxide reference (solid inorganic adjuvant used in veterinary and human medicine). The titers are given 14/28/42/56/90 days after the date of the first injections, for the humoral (IGG1) and cellular (IGG2) response. A second injection of the formulas is made at 28 days, after recording of the antibody titers. The results for the long-term response (90 days) indicate a strong correlation between the low values of the heavy fraction and the intensity of the humoral response at 90 days. The response is significantly reduced when this fraction is greater than 4.7% (7.1% and 9.6%).

These results demonstrate that a mineral oil for a vaccine adjuvant in the form of a W/O emulsion containing less than 10% SF, less than 5% HF and a P/N ratio greater than or equal to 1.9 induces a good cellular type response.

TABLE 3

Antibody response of the IgG1 type against OVA in mice for various oils after injection in the form of a W/O emulsion as a function of time.

| OIL REF | SF (<C16) | MD | HF (>C28) | P/N | D14 | D28 | D42 | D56 | D90 |
|---|---|---|---|---|---|---|---|---|---|
| 2 | 4.9 | 21.5 | 7.1 | 1.86 | 9600 | 16 000 | 128 000 | 128 000 | 128 000 |
| 3 | 4.2 | 20.5 | 1.5 | 1.86 | 9600 | 16 000 | 128 000 | 256 000 | 256 000 |
| 4 | 4.4 | 21.6 | 4.7 | 1.86 | 9600 | 16 000 | 128 000 | 256 000 | 256 000 |
| 6 | 0.3 | 22.2 | 9.6 | 2.03 | 9600 | 16 000 | 64 000 | 64 000 | 64 000 |
| 9 | 2 | 19.3 | 2.2 | 2.85 | 9600 | 16 000 | 128 000 | 256 000 | 256 000 |
| 11 | 8.6 | 20.7 | 2.4 | 1.94 | 9600 | 16 000 | 128 000 | 256 000 | 256 000 |
| AlOH | | | | | 16 000 | 4 800 | 4 800 | 2400 | 2400 |

TABLE 4

Antibody response of the IgG2 type against OVA in mice for various oils after injection in the form of a W/O emulsion.

| Oil Ref | SF (<C16) | MD | HF (>C28) | P/N | D14 | D28 | D42 | D56 | D90 |
|---|---|---|---|---|---|---|---|---|---|
| 2 | 4.9 | 21.5 | 7.1 | 1.86 | 9600 | 16 000 | 48 000 | 48 000 | 48 000 |
| 3 | 4.2 | 20.5 | 1.5 | 1.86 | 9600 | 16 000 | 48 000 | 48 000 | 48 000 |
| 4 | 4.4 | 21.6 | 4.7 | 1.86 | 9600 | 16 000 | 48 000 | 48 000 | 48 000 |
| 6 | 0.3 | 22.2 | 9.6 | 2.03 | 9600 | 16 000 | 128 000 | 256 000 | 256 000 |
| 9 | 2 | 19.3 | 2.2 | 2.85 | 9600 | 16 000 | 128 000 | 256 000 | 256 000 |
| 11 | 8.6 | 20.7 | 2.4 | 1.94 | 9600 | 16 000 | 128 000 | 256 000 | 256 000 |
| AlOH | | | | | 16 000 | 4800 | 4800 | 2400 | 2400 |

Study in the Form of an Aqueous Continuous Phase Emulsion

Two galenic types representing aqueous continuous phase emulsions (W/O/W multiple emulsion and O/W microemulsion) were tested.

Oil-in-Water Microemulsion:

The adjuvant formula comprises, for 100% of its mass, 40 mass % of a hydrophilic surfactant (polysorbate 80) and 60 mass % of mineral oil to be tested; the oily phase thus formulated is emulsified at room temperature by a high-pressure homogenizer in the presence of an aqueous phase comprising the antigen (OVA); the oily phase previously prepared is used at 10 mass % in the final vaccine composition (OVA 10 μg/dose, 100 μl per injection); a control on aluminum hydroxide is included in the trial. The results are presented in table 5. The low intensity of the IGG1 response is directly correlated with the presence of HF, which inhibits the short-term response (28 days, D28) and the long-term response (90 days, D90).

Likewise, table 6 presents the IGG2 titers.

The results show a correlation between the P/N ratio and the IGG2 response; the formulas 6 and 9 stand out from the other products.

TABLE 5

Antibody response of the IgG1 type against OVA in mice for various oils in the form of an O/W microemulsion as a function of time.

| OIL REF | SF (<C16) | MD | HF (>C28) | P/N | D14 | D28 | D42 | D56 | D90 |
|---|---|---|---|---|---|---|---|---|---|
| 2 | 4.9 | 21.5 | 7.1 | 1.9 | 12 800 | 16 000 | 96 000 | 48 000 | 48 000 |
| 3 | 4.2 | 20.5 | 1.5 | 1.9 | 9600 | 48 000 | 128 000 | 256 000 | 256 000 |
| 4 | 4.4 | 21.6 | 4.7 | 1.9 | 12800 | 48 000 | 128 000 | 128 000 | 128 000 |
| 6 | 0.3 | 22.2 | 9.6 | 2.0 | 4800 | 16 000 | 48 000 | 48 000 | 32 000 |
| 9 | 2.0 | 19.3 | 2.2 | 2.8 | 6400 | 48 000 | 32 000 | 128 000 | 128 000 |
| 11 | 8.6 | 20.7 | 2.4 | 1.9 | 9600 | 48 000 | 128 000 | 256 000 | 256 000 |
| AlOH | | | | | 16 000 | 4800 | 4800 | 2400 | 2400 |

TABLE 6

Antibody response of the IgG2 type against OVA in mice for various oils in the form of an O/W microemulsion as a function of time.

| OIL REF | SF (<C16) | MD | HF (>C28) | P/N | D14 | D28 | D42 | D56 | D90 |
|---|---|---|---|---|---|---|---|---|---|
| 2 | 4.9 | 21.5 | 7.1 | 1.86 | 400 | 12000 | 24 000 | 4000 | 400 |
| 3 | 4.2 | 20.5 | 1.5 | 1.86 | 600 | 16000 | 24 000 | 1000 | 1000 |
| 4 | 4.4 | 21.6 | 4.7 | 1.86 | 150 | 8000 | 8000 | 1000 | 1000 |

TABLE 6-continued

Antibody response of the IgG2 type against OVA in mice for various oils in the form of an O/W microemulsion as a function of time.

| OIL REF | SF (<C16) | MD | HF (>C28) | P/N | D14 | D28 | D42 | D56 | D90 |
|---|---|---|---|---|---|---|---|---|---|
| 6 | 0.3 | 22.2 | 9.6 | 2.03 | 4800 | 16000 | 32 000 | 8000 | 4000 |
| 9 | 2 | 19.3 | 2.2 | 2.85 | 1600 | 32000 | 48 000 | 96 000 | 96000 |
| 11 | 8.6 | 20.7 | 2.4 | 1.94 | 600 | 16000 | 24 000 | 1000 | 4000 |
| AlOH | | | | | 150 | 150 | 150 | 300 | 300 |

Comparisons of the IgG1/IgG2 ratios clearly show a difference in behavior in the response for the groups vaccinated with oil 9 and to a lesser degree with oil 6 compared to the other oils (table 7).

TABLE 7

IgG1/IgG2 ratio against OVA in mice for various oils in the form of an O/W microemulsion as a function of time.

| OIL REF | SF (<C16) | MD | HF (>C28) | P/N | D14 | D28 | D42 | D56 | D90 |
|---|---|---|---|---|---|---|---|---|---|
| 2 | 4.9 | 21.5 | 7.1 | 1.86 | 32 | 1 | 4 | 12 | 120 |
| 3 | 4.2 | 20.5 | 1.5 | 1.86 | 16 | 3 | 5 | 256 | 256 |
| 4 | 4.4 | 21.6 | 4.7 | 1.86 | 85 | 6 | 16 | 128 | 128 |
| 6 | 0.3 | 22.2 | 9.6 | 2.03 | 1 | 1 | 2 | 6 | 8 |
| 9 | 2 | 19.3 | 2.2 | 2.85 | 4 | 2 | 1 | 1 | 1 |
| 11 | 8.6 | 20.7 | 2.4 | 1.94 | 16 | 3 | 5 | 256 | 64 |
| AlOH | | | | | 107 | 32 | 32 | 8 | 8 |

Water-in-Oil-Water (W/O/W) Multiple Emulsion:
The adjuvant formula is this time composed of an anhydromannitol octadecenoate ether with a hydrophilic lipophilic balance (HLB)=9, dispersed at 15 mass % in the mineral oil to be tested. The vaccine composition is prepared by mixing at 30° C. one part by weight of adjuvant with one part by weight of antigenic medium (aqueous phase) comprising the antigen OVA.

Trial on Mice:
the results of the mouse trial for the IGG1 responses and for the IGG2 responses are presented in tables 8 and 9 respectively. As regards the cellular response, the variation of the values for the IGG2 responses shows that oil 9 induces an intense and lasting response, especially after 28 days.

Trial on Bovine Model:
in this case, the same vaccines were tested on 5 bovines injected with 2 ml subcutaneously; formulas 9 and 11 were compared. The results are presented in table 10. No difference is observed for the IGG1 titers (data not shown). A strong adjuvant effect is observed compared with the antigen alone. The IGG2 response is very intense with oil 9, low with oil 11 and inexistent for the antigen alone.

TABLE 8

Antibody response of the IgG1 type against OVA in mice for various oils in the form of a W/O/W emulsion as a function of time.

| Oil ref | SF (<C16) | MD | HF (>C28) | P/N | D14 | D28 | D42 | D56 | D90 |
|---|---|---|---|---|---|---|---|---|---|
| 2.0 | 4.9 | 21.5 | 7.1 | 1.9 | 16000 | 32000 | 64000 | 64000 | 64000 |
| 3.0 | 4.2 | 20.5 | 1.5 | 1.9 | 16000 | 64000 | 128000 | 128000 | 128000 |
| 4.0 | 4.4 | 21.6 | 4.7 | 1.9 | 16000 | 64000 | 128000 | 128000 | 128000 |
| 6.0 | 0.3 | 22.2 | 9.6 | 2.0 | 16 000 | 64000 | 64 000 | 64 000 | 64000 |
| 9.0 | 2.0 | 19.3 | 2.2 | 2.8 | 16 000 | 64000 | 128000 | 128000 | 128000 |
| 11.0 | 8.6 | 20.7 | 2.4 | 1.9 | 16 000 | 64000 | 128000 | 128000 | 128000 |
| AlOH | | | | | 16 000 | 4800 | 4800 | 2400 | 2400 |

TABLE 9

Antibody response of the IgG2 type against OVA in mice for various oils in the form of a W/O/W emulsion as a function of time.

| Oil ref | SF (<C16) | MD | HF (>C28) | P/N | D14 | D28 | D42 | D56 | D90 |
|---|---|---|---|---|---|---|---|---|---|
| 2 | 4.9 | 21.5 | 7.1 | 1.86 | 400 | 12 000 | 24 000 | 4000 | 400 |
| 3 | 4.2 | 20.5 | 1.5 | 1.86 | 400 | 12 000 | 24 000 | 4000 | 400 |
| 4 | 4.4 | 21.6 | 4.7 | 1.86 | 400 | 12 000 | 24 000 | 4000 | 400 |

TABLE 9-continued

Antibody response of the IgG2 type against OVA in mice for various oils in the form of a W/O/W emulsion as a function of time.

| Oil ref | SF (<C16) | MD | HF (>C28) | P/N | D14 | D28 | D42 | D56 | D90 |
|---|---|---|---|---|---|---|---|---|---|
| 6 | 0.3 | 22.2 | 9.6 | 2.03 | 400 | 4 000 | 12 000 | 4000 | 400 |
| 9 | 2 | 19.3 | 2.2 | 2.85 | 9600 | 16 000 | 128 000 | 256000 | 256000 |
| 11 | 8.6 | 20.7 | 2.4 | 1.94 | 300 | 600 | 1 200 | 1200 | 1200 |
| AlOH | | | | | 150 | 150 | 150 | 300 | 300 |

TABLE 10

Antibody response of the IgG2A type against OVA in bovines for oils 9 and 11, in the form of a W/O/W emulsion as a function of time.

| Oil ref | SF (<C16) | MD | HF (>C28) | P/N | D0 | D28 | D60 | D140 |
|---|---|---|---|---|---|---|---|---|
| 9 | 2 | 19.3 | 2.2 | 2.85 | — | 600 | 6 000 | 10 000 |
| 11 | 8.6 | 20.7 | 2.4 | 1.94 | — | 10 | 600 | 2 000 |

To improve the cellular component of the immune response, it is sought:
A) to obtain an immune response which is characterized by an IgG1/IgG2 ratio between 0.25 and 4, and
B) to obtain an immune response whose cellular component is also intense, namely characterized by an IgG2 greater than or equal to 32 000 after the vaccination booster administered after 28 days and after measuring the IGG2 titer on this date (secondary and long-term response).

A—IgG1/IgG2 Ratio
a) case of the vaccine adjuvants which are in the form of a w/o/w emulsion, the IgG1/IgG2 experimental results are as follows:
  for oil 6: 40 (D14), 16 (D28), 5.3 (D42), 16 (D56) and 160 (D90).
  for oil 11: 53.3 (D14), 107 (D28), 107 (D42), 107 (D56) and 107 (D90).
  for oil 9: 1.7 (D14), 4 (D28), 1 (D42), 0.5 (D56) and 0.5 (D90).
Oil 9 makes it possible to obtain an IgG1/IgG2 ratio between 0.25 and 4 before and after the vaccination booster on D28 (the vaccination booster made on D28, is administered after measuring the immune response).
b) case of the vaccine adjuvants which are in the form of an O/W microemulsion, the statement of invention comprises the following IgG1/IgG2 experimental results:
  for oil 6: 1 (D14), 1 (D28), 2 (D42), 6 (D56) and 8 (D90)
  for oil 11: 16 (D14), 3 (D28), 5 (D42), 256 (D56) and 64 (D90)
  for oil 9: 4 (D14), 2 (D28), 1 (D42), 1 (D56) and 1 (D90)
For oil 9, the IgG1/IgG2 ratio between 0.25 and 4 is still obtained before the vaccination booster on D28 and remains constant over time.
For oil 6, the IgG1/IgG2 ratio between 0.25 and 4 is also obtained before the vaccination booster (primary response) but does not last over time during the measurement of the secondary response (after the vaccination booster of D28) and of the long-term response (D90).
For oil 11, the IgG1/IgG2 ratio between 0.25 and 4 is not observed for the secondary response or for the long-term response.
c) case of the vaccine adjuvants which are in the form of a W/O emulsion, the statement of invention comprises the following IgG1/IgG2 experimental results:
  for oil 9: 1 (D14), 1 (D28), 1 (D42), 1 (D56) and 1 (D90)
All these recorded results show good results for the IgG1/IgG2 ratio.

B—Intensity of the IgG2 responses
a) case of the vaccine adjuvants which are in the form of a W/O/W emulsion, the IgG2 experimental results are as follows (table 9):
  a. for oil 6 (D14), 4 000 (D28), 12 000 (D42), 4 000 (D56) and 400 (D90)
  b. for oil 11: 300 (D14), 600 (D28), 1200 (D42), 1200 (D56) and 1200 (D90)
  c. for oil 9: 9600 (D14), 16 000 (D28), 128 000 (D42), 256 000 (D56) and 256 000 (D90)
Oil 9 makes it possible to obtain an intense cellular response (according to the criteria previously defined) after the vaccination booster administered after 28 days.
b) case of the vaccine adjuvants which are in the form of an O/W microemulsion, the statement of invention comprises the following IgG2 experimental results (table 6):
  a. for oil 6: 4800 (D14), 16 000 (D28), 32 000 (D42), 8 000 (D56) and 4000 (D90)
  b. for oil 11: 600 (D14), 16 000 (D28), 24 000 (D42), 1000 (D56) and 40 000 (D90)
  c. for oil 9: 1600 (D14), 32 000 (D28), 48 000 (D42), 96 000 (D56) and 96 000 (D90)
Oil 9 makes it possible to have an intense cellular response (according to the criteria previously defined) for the secondary response (after the vaccination booster) and for the long-term response (D90).
c) case of the vaccine adjuvants which are in the form of a W/O emulsion, the statement of invention comprises the following IgG2 experimental results (tableau 4):
  a. for oil 9: 9600 (D14), 16 000 (D28), 128 000 (D42), 256 000 (D56) and 256 000 (D90)
All these recorded results show good results for the IgG2 response.
According to these results, it is clearly shown that a composition of a mineral oil intended to be used as injectable vaccine adjuvant, which is the subject of the present invention, such as oil 9 for example, having the following characteristics:
  SF<10% and HF<5%;
  P/N between 2.5 and 3 (about 2.85 here);
ensures good safety, good efficacy as for the humoral response and a strong cellular response both in the form of a W/O and W/O/W emulsion and O/W microemulsion.

II) Part Two

Trial Series 1: Experimental Work on a "Chicken" Model
In the context of the experimental trials used, the efficacy of the response for each formula is based on the following criteria:

a) antibody titer in the sera;
b) infiltration of white cells at the site of injection;
c) virulence challenge consisting in inoculating animals with 10 000 oocysts of the *Emeria acervulina* strain two weeks after treatment, and comparing:
   a. the weight gain by the animals
   b. the number of parasites excreted Table 11 shows the various formulas which were tested:

TABLE 11

| | GROUP | | | | | |
|---|---|---|---|---|---|---|
| | A | B | C | D | E | F |
| EMULSION | W/O | W/O | W/O/W | W/O/W | CFA | without emulsion |
| OIL | 1 | 2 | 1 | 2 | standard mineral | without oil |

The oils involved in the experimental trials are characterized in the table below

| Oil Ref | SF (<C16) | MD | HF (>C28) | P/N | LR |
|---|---|---|---|---|---|
| Standard mineral | 4.9 | 21.5 | 7.1 | 1.86 | 0.5 |
| Oil 1 (O1) | 2 | 19.3 | 2.2 | 2.85 | 0 |
| Oil 2 (O2) | 8.6 | 20.7 | 2.4 | 1.94 | 0.5 |

The formulations for groups A and B, namely the W/O1 emulsions (Group A) and the W/O2 emulsions (Group B), comprise for 100% of their mass:
  30 mass % of an aqueous phase comprising the antigen and water
  70 mass % of oily adjuvant comprising for 100% of its mass:
    15 mass % of mannitan oleate
    85 mass % of oil (Oil 1 or Oil 2)

The antigen, protein 3-1 E, is present in these formulations in a proportion such that a dose of formulation injected comprises 50 µg of antigen, the volume of the dose of formulation injected being 100 µL.

The formulations for groups C and D, namely the W/O1/W microemulsions (Group C) and the W/O2/W microemulsions (Group D) comprise for 100% of their mass:
  90 mass % of an aqueous phase comprising the antigen and water
  mass % of oily adjuvant comprising for 100% of its mass:
    40 mass % of ethoxylated sorbitan oleate containing 20 moles of ethylene oxide (Polysorbate 80)
    60 mass % of oil (Oil 1 or Oil 2).

The antigen, protein 3-1 E, is (are) present in these formulations in a proportion such that a dose of formulation injected comprises 50 µg of antigen, the volume of the dose of formulation injected being 100 µL.

In the case of the antibody titers in the sera, all the groups tested had high and equivalent serum antibody titers except the group having the protein alone (Group F). The humoral response obtained for each of the groups is at a high and satisfactory level (results not shown).

In the case of the infiltrations of white cells at the site of injection, the intensities of local infiltrations of said white cells (lymphocytes and macrophages) were evaluated by indirect immunofluorescence on tissue sections for the various groups.

Biopsies were performed on 3 animals of each group, at the site of injection, so as to obtain skin samples from these animals. This biopsy was performed a day after the second immunization of said animals, that is 28 days after the first immunization. These immunizations consisted in injections of a mixture of profilin and formulations tested. A control, consisting in an injection of profilin without vaccine medium, was also carried out under the same operating conditions. The samples thus obtained were immediately frozen in a medium containing liquid nitrogen and stored at a temperature of −20° C. Pieces of 5 µm of each sample were then placed on supports that had been cleaned beforehand, and washed in acetone for 20 minutes at a temperature of 4° C., and "fixed" with 10% horse serum for 20 minutes at a temperature of 20° C. Chicken CD8 antibodies, diluted 1/200, were added and then the mixture resulting therefrom was incubated at room temperature (20° C.) for 2 hours. The supports were then washed with a phosphate buffer solution and incubated with a chicken IgG secondary antibody "Alexa Fluor 488-labeled antichicken" (marketed under the name Invitrogen by the company Carlsbad) at a dilution of 1/500 for 2 hours at room temperature (20° C.). The supports were then brought into contact with a colorimetric indicator, Fluoromount-G, and examined with an electron microscope (marketed under the name LSM 510 META by the company Carl Zeiss).

Using this protocol, visualization of the CD8+ cells was assessed by a score according to the following scale:
  score "0": absence of spots of CD8+ cells observed,
  score "+": observation of a presence, of a low density, of CD8+ cells,
  score "++": observation of a strong presence, of a high density, of CD8+ cells, and
  score "+++": observation of a very strong presence, of a very high density, of CD8+ cells.

The higher the quantity and density of lymphocytes and macrophages observed at the site of injection, the greater the capacity for the vaccine tested to develop an effective immune response.

The results obtained are shown in the table 12

TABLE 12

| | GROUP | | | | | |
|---|---|---|---|---|---|---|
| | A | B | C | D | E | F |
| Adjuvant | W/O1 | W/O2 | W/O1/W | W/O2/W | CFA | WITHOUT ADJUVANT |
| Antigen | yes | yes | yes | yes | yes | yes |
| Lymphocyte | +++ | + | ++ | ++ | + | 0 |
| Macrophage | ++ | + | + | + | + | 0 |

Compared with the vaccine comprising the adjuvant of the state of the art (Group E), the vaccines according to the invention improve the production of lymphocytes at the site of injection for groups D, C and A; whereas for the macrophages, only the vaccine according to the invention of group A makes it possible to improve the production of macrophages and the other vaccines according to the invention make it possible to obtain results for the production of macrophages at the site of injection similar to the vaccine comprising the adjuvant of the state of the art.

In the case of the virulence challenge, an effective protection by the vaccine will mean that the animals:

will exhibit a similar weight gain compared with the nonvaccinated and nonchallenged controls;

will exhibit a reduction in the parasite load (evaluated by the number of parasites excreted) compared with the challenged and nonvaccinated animals.

In general, the virulent challenge corresponds to the administration of a precise and controlled dose of pathogenic agent against which the animals have previously been vaccinated. The protection induced by the experimental vaccines is evaluated according to various criteria as a function of the animal model and the nature of the pathogen.

Two main criteria were monitored post-virulent challenge: weight gain by the animals 10 days post-infection, and reduction in the number of pathogens excreted.

Weight Gain by the Animals 10 Days Post-Infection.

Tableau 13 summarizes the results obtained during vaccination and infection of chicken against avian coccidiosis (strain used *Emeria acervulina*). The pathogenicity of this strain is high and results in a modification of the weight gain by the animals infected.

TABLE 13 weight gain for the different groups after virulent challenge.

| | GROUP | | | | | | |
|---|---|---|---|---|---|---|---|
| | A | B | C | D | E | F | G | H |
| EMULSION | W/O1 | W/O2 | W/O1/W | W/O2/W | CFA | WITHOUT ADJUVANT | WITHOUT VACCINE | WITHOUT VACCINE |
| Antigen | yes | yes | yes | yes | yes | yes | No | No |
| VIRULENT CHALLENGE | | | 10 000 *Emeria acervulina* oocysts | | | | | WITHOUT CHALLENGE |
| WEIGHT GAIN TEN DAYS AFTER CHALLENGE (g) | 834 | 798 | 802 | 740 | 773 | 735 | 730 | 850 |

It can be seen that for challenged subjects, vaccination without adjuvant does not induce protection in terms of weight gain: since the controls without adjuvant (Group F) and without vaccine (Group G) induce similar results.

Compared with the challenged and nonvaccinated subjects (group G), the vaccines according to the invention comprising an adjuvant based on oils O1 and O2 allow significant weight gains with the exception of the vaccines of Group D.

Compared with the vaccine comprising the adjuvant of the state of the art (Group E), the vaccines according to the invention induce a higher weight gain with the exception of the vaccine which is in the form of a W/O2/W emulsion (Group D).

It should also be noted that the vaccines according to the invention comprising an adjuvant based on oil 1 induce a higher weight gain than the vaccines according to the invention comprising an adjuvant based on oil 2.

For the vaccines according to the invention of group A, the weight gain is only 1.9% lower compared with the weight gain of the nonchallenged subjects.

Moreover, for each of the mineral oils considered (O1 or O2), it will be noted that the experimental vaccines formulated as a water/oil emulsion appear to be more protective than the water/oil/water formulas:

for oil 1, the weight gain for a vaccine in the form of a W/O1 emulsion (group A) is 834 g, that is a weight gain of 99 g compared with the animals of the group without adjuvant (group F), whereas for a vaccine in the form of a W/O1/W emulsion, the weight gain (group C) is 802 grams and gives a weight gain of 67 g compared with the animals of the group without adjuvant (group F).

for oil 2, the weight gain for the vaccine in the form of a W/O2 emulsion (group B) is 798 g, that is a weight gain of 63 g compared with the animals of the group without adjuvant (group F) whereas for a vaccine in the form of a W/O2/W emulsion, the weight gain (group D) is 740 grams, and gives a weight gain of 5 g compared with the animals of the group without adjuvant (group F).

Reduction in the Number of Excreted Pathogens:

The results obtained are presented in table 14.

The results are expressed as a reduction in the number of excreted oocysts (the more the animals are infected, the more they excrete, therefore the less they were protected).

TABLE 14

| | GROUP | | | | | |
|---|---|---|---|---|---|---|
| | A | B | C | D | E | F |
| Adjuvant | W/O1 | W/O2 | W/O1/W | W/O2/W | CFA | WITHOUT ADJUVANT |
| Antigen | yes | yes | yes | yes | yes | yes |
| Mean excreted (×10E8) | 1.42 | 2.75 | 2.54 | 3.09 | 2.13 | 2.86 |
| STANDARD DEVIATION | 0.23 | 0.52 | 0.8 | 0.39 | 0.49 | 0.36 |

Compared with the control in group F (antigen but without adjuvant), the vaccines according to the invention therefore induce a reduction in the mean excreted.

Compared with Group E (antigen+adjuvant of the state of the art), the vaccine according to the invention of group 1 gives a reduction in the mean excreted.

Furthermore, the standard deviation for Group A is the lowest, indicating a more homogeneous response of the animals vaccinated. This criterion is an important point because it means that the individual sensitivities in biological response of the animals are smoothed out by the efficacy of the vaccine.

Conclusion Trial 1

The vaccines comprising the adjuvants according to the invention make it possible to provide an improved immune response and a greater efficacy for protecting poultry from coccidiosis.

Moreover, the vaccine according to the invention which is in the form of a W/O1 emulsion, with O1 characterized by a P/N ratio>2, has the advantage of stimulating a higher production of white cells at the site of injection, and of reconciling, following a virulence challenge with the *Emeria acervulina* strain, both the highest weight gain and a very significant reduction in the excretion of oocysts.

*E. acervulina*: it is moderately pathogenic.

The lesions are located in the small intestine, especially in the duodenum, with whitish spots and then streaks in the mucous membrane="scaled" lesions. The lesions are caused by the oocysts.

*E. tenella*: it is the most pathogenic coccidia, the lesions being caused by schizonts.

The lesions are located in the ceca, which are filled with blood, can rupture or be gangrenous. The carcass may be anemic. The mortality is often high.

Table 15 describes the various groups tested:

TABLE 15

| | GROUPE | | | | | | | | |
|---|---|---|---|---|---|---|---|---|---|
| | A | B | C | D | E | F | G | H | I |
| Description | not vaccinated | not vaccinated | not vaccinated | vaccinated | vaccinated | vaccinated | vaccinated | vaccinated | vaccinated |
| Antigen 3-1 E (30 µg/ml) | no | no | no | yes | yes | yes | yes | yes | yes |
| Adjuvant | not vaccinated | not vaccinated | not vaccinated | no | no | CFA | CFA | W/O1 | W/O1 |
| Virulence challenge strain | not challenged | EA | ET | EA | ET | EA | ET | EA | ET |

CFA: Complete Freund's Adjuvant (adjuvant of the state of the art)

Trial Series 2:
Taking into account TRIAL series 1 and its conclusions, namely the observation of better performance for a vaccine comprising:
  the recombinant protein comprising the Eimera acervulina sequence 3-1
  oil 1
  water
  a surfactant system
and provided in the form of a W/O emulsion, the inventors carried out two types of virulence challenge:
  a virulence challenge with the *Emeria acervulina* (AE) strain,
  a virulence challenge with the *Emeria tenella* (ET) strain.
The formulations tested, namely the W/01 emulsions, comprise for 100% of their mass:
  mass % of an aqueous phase comprising the antigen and water
  70 mass % of oily adjuvant comprising for 100% of its mass:
  15 mass % of mannitan oleate;
  85 mass % of oil (Oil 1 or Oil 2).
The antigen, protein 3-1 E, is present in these formulations in a proportion such that a formulation dose injected comprises 30 µg of antigen, the volume of formulation dose injected being 100 µL.

To identify cross-protections broadening the properties of the experimental vaccine tested. Indeed, the induced immune response of the cellular type thus makes it possible to protect against various strains of parasites.

The protein dose used is 30 µg/ml. The virulent challenge is performed by administering 10 000 oocysts per bird (table 15).

The animals are then monitored on the parameters of weight gain, antibody, proliferation of spleen lymphocytes after antigenic restimulation or with mitogens (in order to quantify the cellular response) and protection during a virulent challenge.

The vaccinated chickens in the various groups are then monitored according to the following different criteria:
  a) weight gain;
  b) production of antibody titers (serology);
  c) evaluation of the intensities of the local infiltrations of white cells (lymphocytes) by the indirect immunofluorescence method on samples of spleen splenocytes taken 48 h after the vaccination (or immunization). These immunizations consist in injections of a mixture of profilin and the formulations tested. A control, consisting in an injection of profilin without vaccine medium, was also made under the same operating conditions. The procedure used is identical to that used on the skin samples from the animals, which is described above, namely:
    preservation of the splenocyte samples collected, at −20° C.
    placing of the splenocyte samples on supports and washing in acetone for 20 minutes at 20° C.
    addition of CD8 antibodies diluted 1/200 and subsequent incubation for 2 hours at 20° C.
    washing of the supports obtained with a phosphate buffer solution, and subsequent incubation with a chicken IgG secondary antibody "Alexa Fluor 488-labeled antichicken" at a dilution of 1/500 for 2 hours at room temperature (20° C.)
    contacting with the colorimetric indicator Fluoromount-G
    examination with an electron microscope (marketed under the name LSM 510 META by the company Carl Zeiss).
Using this protocol, visualization of the CD8+ cells lymphocytes was assessed by a score according to the following scale:
  score "0": absence of spots of CD8+ cells observed,
  score "+": observation of a presence, of a low density, of CD8+ cells, score "++": observation of a strong presence, of a high density, of CD8+ cells, and score "+++": observation of a very strong presence, of a very high density, of CD8+ cells;

d) number of oocysts excreted.

Results:

weight gain: the groups vaccinated with the vaccine which is in the form of a W/O1 emulsion are characterized by a weight gain similar to that observed for the other groups (results not shown);

serology: high production of antibody titers, higher than that observed for the groups vaccinated with the vaccine having CFA as adjuvant and than that observed for the groups vaccinated with a vaccine having no adjuvant (results not shown);

proliferation of the lymphocytes: the highest scores are obtained for the groups H and I vaccinated with the vaccine which is in the W/0 form and which comprises the adjuvant with oil O1.

| | GROUP | | | | | | | | |
|---|---|---|---|---|---|---|---|---|---|
| | A | B | C | D | E | F | G | H | I |
| Lymphocyte proliferation index | 0 | 0 | 0 | 0 | 0 | 0 | 0 | ++ | ++ | number of oocysts excreted:

Tables 16 and 17 show the results of the number of oocysts excreted for the groups that were subjected to the virulence challenge with *Emeria acervulina* and *Emeria tenella* respectively.

TABLE 16

Results of excretion after virulent challenge with the EA strain

| GROUP | B | D | F | H |
|---|---|---|---|---|
| Mean (×10E8) | 3.44 | 3.33 | 3.30 | 2.71 |
| Standard deviation | 0.50 | 0.67 | 0.89 | 0.27 |

TABLE 17

Results of excretion after virulent challenge with the ET strain.

| GROUP | C | E | G | I |
|---|---|---|---|---|
| Mean (×10E8) | 1.49 | 1.20 | 1.11 | 0.95 |
| Standard deviation | 0.23 | 0.27 | 0.42 | 0.13 |

For both strains, the groups vaccinated with the vaccine comprising the adjuvant based on O1 show an excretion mean that is lower than that observed on the groups vaccinated with the vaccine comprising the adjuvant of the state of the art (CFA). The same is true of the comparison with the groups vaccinated with a vaccine containing no adjuvant (groups D and E).

The invention claimed is:

1. A vaccine adjuvant for 100% of its mass comprising:
   from 10% to 95% of a mineral oil comprising:
      from 0.05 mass % to 10 mass % of hydrocarbon chains having less than 16 carbon atoms;
      from 0.05 mass % to 5 mass % of hydrocarbon chains having more than 28 carbon atoms;
      and having a P/N ratio, corresponding to the ratio between the quantity by mass of hydrocarbon chains of the paraffin type and the quantity by mass of hydrocarbon chains of the naphthene type, of between 2.5 and 3; and
   from 5% to 90% of at least one surfactant.

2. The adjuvant as claimed in claim 1, wherein said P/N ratio is between 2.8 and 2.9.

* * * * *